(12) United States Patent
Simmoteit et al.

(10) Patent No.: US 7,175,852 B2
(45) Date of Patent: Feb. 13, 2007

(54) IMPLANT AND PROCESS FOR PRODUCING IT

(75) Inventors: Robert Simmoteit, Rangendingen (DE); Heike Fisher geb. Schoof, Reutlingen (DE)

(73) Assignee: Jotec GmbH, Hechigen (DE)

(*) Notice: Subject to any disclaimer, the term of this patent is extended or adjusted under 35 U.S.C. 154(b) by 259 days.

(21) Appl. No.: 10/191,674

(22) Filed: Jul. 9, 2002

(65) Prior Publication Data
US 2003/0023318 A1 Jan. 30, 2003

(30) Foreign Application Priority Data
Jul. 13, 2001 (DE) .............................. 101 35 275

(51) Int. Cl.
*A61F 2/02* (2006.01)
*A61F 2/04* (2006.01)

(52) U.S. Cl. ............. 424/423; 623/11.11; 623/23.64; 623/23.74; 623/23.75

(58) Field of Classification Search ............... 435/180, 435/182; 424/426, 423; 623/1.38, 1.41, 623/1.47, 11.11, 23.64, 23.74, 23.75
See application file for complete search history.

(56) References Cited

U.S. PATENT DOCUMENTS

| | | | |
|---|---|---|---|
| 4,280,954 A * | 7/1981 | Yannas et al. | 530/356 |
| 4,787,900 A | 11/1988 | Yannas | |
| 4,955,893 A * | 9/1990 | Yannas et al. | 606/154 |
| 5,716,411 A | 2/1998 | Orgill et al. | |
| 6,015,844 A * | 1/2000 | Harvey et al. | 523/113 |
| 6,162,887 A * | 12/2000 | Yamada et al. | 526/351 |

FOREIGN PATENT DOCUMENTS

| | | |
|---|---|---|
| DE | 32 03957 A1 | 8/1983 |
| DE | 691 10 787 | 4/1996 |
| EP | 0 562 864 A1 | 9/1993 |
| EP | 470 246 | 6/1995 |
| JP | 08024326 | 1/1996 |
| WO | WO 92/10217 | 6/1992 |
| WO | WO 99/27315 | 6/1999 |
| WO | WO 00/01432 | 1/2000 |
| WO | WO 00/38590 | 7/2000 |
| WO | WO 00/47129 | 8/2000 |
| WO | WO 200047129 A2 * | 8/2000 |

OTHER PUBLICATIONS

Matsumoto et al., "Peripheral nerve regeneration across an 80-mm gap bridged by a polyglycolic acid (PGA)-collagen tube filled with laminin-coated collagen fibers: a historical & electrophysiological evaluation . . . ," Brain Research 868:315-328, 2000.*
Ladon, "Chemical equilibrium-solubility," http://www.towson.edu/~ladon / solprod.html, 2001.*

* cited by examiner

*Primary Examiner*—Robert A. Wax
*Assistant Examiner*—Rosanne Kosson
(74) *Attorney, Agent, or Firm*—Harness, Dickey & Pierce, P.L.C.

(57) ABSTRACT

The invention relates to a process for producing an implant, with the implant possessing a textured foreign structure. A porous protein matrix is at least partially anchored in the textured foreign structure, with the porous protein matrix possessing a directional pore structure.

12 Claims, 3 Drawing Sheets

IMPLANT AND PROCESS FOR PRODUCING IT

BACKGROUND OF THE INVENTION

1. Field of the Invention

The invention relates to an implant and to a process for producing it.

2. Related Prior Art

Implants, and processes for producing them, have been frequently disclosed in the prior art.

Implantable structures in combination with cells are used, in particular, in the field of tissue engineering, an interdisciplinary field of research which is concerned with methods and materials for producing "artificial" tissue and organ systems. Thus, it is possible to use artificially produced implants as, for example, replacements for skin, bone, cartilage, lenses or as vascular grafts.

In vascular surgery, small-lumen implants are used, in particular, when it is not possible to use a patient's own blood vessels. This is the case, for example, when a specific blood vessel length is required or when the autologous blood vessels cannot be used because of their pathophysiological properties. In this connection, use is made of vascular grafts made of synthetic material, with use being made, in particular, of synthetic materials such as knitted threads of polyethylene terephthalate (PET), (trade name: Dacron), or of expanded polytetrafluoroethylene (ePTFE).

Preference is given to using vascular grafts made out of these synthetic materials since they possess advantageous structural and biocompatible properties. Thus, surrounding tissue can ingrow, on the one hand, and, on the other hand, no blood plasma may escape through the pores. In the case of the ePTFE implants, this is achieved by the adjusted size of the pores, whereas knitted PET implants are impregnated by being coated with resorbable material, such as collagen or gelatin. After implantation, the coating is resorbed to the extent that the surrounding, newly formed tissue grows into the porous collagen layer.

If use is made of synthetic materials which are one-sidedly collagen-coated on the outside, there is a great danger, for example in the case of small-lumen vascular grafts, that the exposed foreign surface of the internal lumen will induce blood coagulation and that the implanted vessel will very rapidly become occluded. This is because the coagulation system, the complement system and the immune system can be activated, in particular, by slowly flowing blood coming into contact with synthetic surfaces.

Consequently, prostheses of this nature cannot be used in the small-lumen vessel range ($\phi < 6$ mm) since, in this range, there is a danger of the vessel rapidly becoming occluded.

More advanced approaches to avoiding blood coagulation are directed towards colonizing the coated implants with cells, such as endothelial cells or fibroblasts.

Endothelial cells line the surface of human blood vessels. Seeding the lumen of vascular grafts with endothelial cells presents the flowing blood with a surface whose coagulation-activating and complement-activating properties are markedly reduced. Coculturing vascular grafts with fibroblasts and endothelial cells, as demonstrated, for example, in PCT 98/01782, improves the ability of the implant to grow into the surrounding tissue and stabilizes the endothelial cell layer in the internal lumen.

Consequently, the interaction of the various cell types which are present, for example, in natural vessels is of importance for the ability of the implants to function. In addition to a high degree of biocompatibility, care must also be taken to ensure that the structure of the implant is adapted to the requirements of different cells.

Another developmental approach is to use acellularized blood vessels of animal origin. In U.S. Pat. No. 5,899,936, these vessels are seeded, after their cellular components have been removed, with autologous cells and then implanted.

A particular disadvantage of these developments is the fact that the implants cannot be produced such that they are adapted to the patient but, instead, are predetermined by the donor animal with regard to the length and size of the vessel. Furthermore, the risks of a disease being transferred by viruses or prions by way of such tissues are not completely resolved.

Another disadvantage is that it is not possible to embed an additional supporting structure into an implant which has been produced in this way in order to increase its stability. In addition, acellularized structures are only relatively storable. Furthermore, the latest debate in the field of xenotransplants indicates that technically produced vascular grafts are preferred.

Recent experimental approaches are directed towards developing completely resorbable implants which are made of synthetic materials such as polyglycolic acid or polylactide. In the context of wound healing, these synthetic materials are replaced with endogenous tissue. An advantage of these implants is that the materials regenerate completely and no synthetic materials, which can give rise to infections, remain in the body. Disadvantages of these implants are the impairment of cell growth during resorption, e.g. as the result of a shift in pH when the polylactide is degraded, and the difficulty in controlling the formation of new tissue, since premature resorption can lead to the implant failing.

WO 00/47129 discloses a method for using a master plate to produce a resorbable membrane which possesses a three-dimensional structure. In this connection, the membrane can also be made of non-resorbable synthetic materials and be coated, where appropriate, with a protein matrix.

This method suffers from the disadvantage that the production of the membrane having a three-dimensional structure is very elaborate. Thus, it is first of all necessary to make the master plates for the different membranes which are required in each case before the supporting structure itself can be produced.

U.S. Pat. No. 4,787,900 discloses a method in which an inner structure made of a resorbable material is coated with an outer layer composed of a material which can also be degraded. At the same time, the two layers can in each case be seeded with cells. A disadvantage of this method is the fact that it is not possible to adapt the outer structure to the particular requirements of the environment into which it is to be implanted. In addition, elaborate steps are involved in the production of the outer layer in this method since, after a freeze-drying process, the outer structure has first of all to be cut back to the desired layer thickness, something which leads to a substantial consumption of material.

Consequently, special mechanical and structural demands are made on implants. Thus, in addition to having adequate structural stability, they must also possess strength and stretching properties which match the tissue which is to be replaced. In addition, implants have to exhibit a variety of fits, lengths and diameters. Furthermore, the microstructuring, such as the inner pore structure, is of importance for seeding with cells and for ingrowing tissue. In addition, the implants should be characterized by the fact that they do not induce any immunological allergies or reactions and by the fact that they are optimally adapted to the particular tissue into which they are implanted.

SUMMARY OF THE INVENTION

One object of the invention is, therefore, to provide an implant and a process for producing it, with the implant being seeded with various cell types and with an encapsulation of the foreign structure or, in the case of a vascular graft, an occlusion, being prevented.

In the process mentioned at the outset, this object is achieved, according to the invention, by the production of an implant which has a textured foreign structure and a porous protein matrix, possessing a directional pore structure, which is at least partly anchored therein.

In addition, an object of the invention is achieved by an implant which possesses a protein matrix, having a directional pore structure, which is at least partially anchored in a textured foreign structure.

The foreign structure can assume various functions, such as a supporting function or the function of a barrier against moisture loss and infection. The latter can, for example, be required in the case of a skin implant. Another possible function of the foreign structure is that of supplying nutrients, in the case of large-lumen implants. For this, the foreign structure can be in the form of a hollow fiber network, or at least contain some hollow fibers.

When the implant according to the invention is seeded with cells, these cells can rapidly migrate along the protein fibers into the matrix since the pore structure and pore size can be adjusted specifically for the given cell type.

The anchoring of the protein matrix possessing a directional pore structure in the foreign structure additionally ensures that the implant as a whole has adequate stability.

In a preferred embodiment of the process according to the invention, a durable synthetic material, which is selected from the group consisting of polytetrafluoroethylene, polyurethane, polystyrene, polyester, ceramic and metals, is used as the textured foreign structure.

In recent years, expanded polytetrafluoroethylene (ePTFE) has become accepted as being the preferred synthetic material for implants. This material is porous and is of such a form that after implantation, the cells are unable to ingrow. In these vascular grafts, which correspond to the state of the art, the nature of the pores also ensures that no (blood) fluid can escape through the pores.

In another preferred embodiment of the process according to the invention, an resorbable synthetic material, which is selected from the group consisting of polylactide, polyglycolic acid, polyhydroxyalkanoates and their copolymers, is used as the textured foreign structure.

In this connection, the possibility is not excluded of also using, as the textured foreign material, other reversible natural materials selected from a group comprising chitin, cellulose, collagen and hydroxyl apatites (calcium phosphate). These materials can, for example, be used as the foreign material in the form of superficially textured film. The calcium phosphate compounds which can be used include, for example apatite, tricalcium phosphate and tetracalcium triphosphate, combined with calcium hydroxide.

Alternatively, the textured foreign structure can be composed of combinations of the abovementioned materials.

The shape of the foreign structure can be chosen at will. The foreign structure can consequently, for example, be chosen to be flat, to act as a skin implant, or be of tubular design, to act as a vascular graft, with it being possible for this tubular version to be shaped in any arbitrary manner, for example as a branched or unbranched tube, etc. For other applications, such as cartilage or bone, the structure can also be designed as a cylinder or a rectangle, or as a heart valve. If the foreign structure comprises hollow fibers, these latter could then be embedded in the protein matrix and serve as conduits for supplying nutrients to cells with which the protein matrix can be seeded.

It is a further object if, in the process according to the invention, the protein matrix is prepared from a suspension, dispersion or paste containing collagen and soluble, non-collagenous constituents.

Collagen is the most frequently occurring protein in the human body and is an essential component of the extracellular matrix of skin, vessels, bones, tendons, cartilage, teeth, etc. The use of native collagen is advantageous since collagen possesses a large number of positive properties when used as a biomaterial.

Non-collagenous accompanying substances can be growth factors or active compounds or other components of the extracellular matrix, such as elastin, laminin, fibronectin, hyaluronic acid or glycosaminoglycans. On the one hand, the soluble constituents comprise acids, such as HCl, acetic acid or ascorbic acid, since the optimum pH range for preparing freeze-dried collagen sponges is known to be between 2.5 and 3.5. On the other hand, it is possible to use soluble additives, such as glycerol or ethanol or finely dispersed additives, such as calcium phosphate, etc., as accompanying substances since their concentration can be used to adjust the ice crystal morphology and consequently the pore structure.

According to a further object of the process according to the invention, the suspension is applied uniformly to the foreign structure and at least partially introduced into it by means of pressure, vacuum or centrifugation.

Applying the suspension uniformly ensures a homogeneous layer thickness, thereby making any subsequent fashioning or cutting to size unnecessary and consequently advantageously saving additional operational steps. In this connection, it is possible to arrange for wall thicknesses of between 0.1 cm and 5 cm. Pressure, vacuum or centrifugation can be adjusted so as to ensure that the suspension is introduced into the textured/porous foreign structure in a controlled manner and down to a given depth. In this connection, it is advantageous if the temperature of the sample is regulated during this process since the viscosity of the suspension depends on the temperature.

According to another object of the process according to the invention, the directional pore structure of the protein matrix is formed by unilaterally cooling one surface and at the same time insulating the other surface. In this connection, the protein suspension is cooled, in a controlled manner, continuously or step-wise on one side with the other side being kept distinct by an insulator, for example air, gases or teflon. During the freezing process, the suspension may partially or completely crystallize. The collagens and dissolved substances are then for the most part displaced by the growing cellular ice-phase front, with the suspended proteins and the dissolved or dispersed substances becoming highly concentrated between the ice crystals. It is possible to use the cooling rate and the chemical composition of the protein suspension to advantageously adjust the ice crystal structure and size at any given layer thickness.

While WO 99/27315 discloses a freezing method, cooling down takes place uniformly on two opposite sides. However, this document states that one-sided cooling is disadvantageous and does not lead to any directional pore structure.

However, as was possible to demonstrate in the process according to the invention, the ice crystals also grow in a directional manner through the sample, virtually parallel to the temperature gradient, during the one-sided freezing process. As a result of the protein suspension being introduced into the foreign structure, the ice crystals also partially grow into the foreign structure.

The directional pore structure is desirable since, in this way, the structure can be optimally matched to the given tissue. Matching the structure and size of the pores improves the migratory behaviour of the surrounding tissue.

In this connection, it is preferred if the size of the pores of the protein matrix is selectively adjusted to between 5 µm and 500 µm.

In a development of the process according to the invention, it is preferred if the sample is freeze-dried after having been cooled.

During the freeze-drying process, the ice crystals sublime, resulting in the formation of cavities, which correspond to the directional pores of the structure. In association with an implantation, the cells of the surrounding tissue can consequently grow into the implant along the protein fibers. As a result of the removal of water during the sublimation, covalent bonds form between the collagen molecules thereby giving the matrix a desired stability. In this connection, it is advantageous that the freeze-drying process, or a chemical treatment of the freeze-dried product, can be used to selectively adjust the degree of crosslinking. The protein matrix which is formed by the freeze-drying process is directly anchored to the foreign structure and no further steps are required for linking the foreign structure to the protein matrix.

It is, furthermore, preferred if the structure is sterilized after the freeze-drying. This is a desirable prerequisite for storing the structures or using them directly.

The structure can now be implanted directly or else, in a preferred embodiment of the process according to the invention, be seeded with cells. The cells which can be used, and subsequently cultured, in this connection, are xenogenic, allogenic or autologous donor cells, stem cells or cell lines. In this connection, this seeding is preferably carried out in a bioreactor under physiological strain, with, depending on the application, a cocultivation of the cell types present in the natural tissue, which cell types can additionally be applied to the structure at different time points, being envisaged.

In this connection, the structure can be cultured until the cells are adhering firmly or else incubated until the resorbed constituents have been broken down or remodelled. The period of culture depends on the particular shape of the structure and on the cells employed.

This has the advantage that vascular grafts, for example, can firstly be provided with an inner epithelial cell layer, resulting in it being possible to avoid thrombogenization and calcification of the implants when autologous donor cells are used, in particular.

In addition, as required, the structure can be loaded or coated with active compounds such as hirudin, aspirin, heparan sulphate, albumin, or the like, prior to the implantation. The release of the active compounds can preferably be controlled by means of a hydrogel coating, which is additionally applied, or by means of the nature of the attachment of the active compounds.

Using simple means, the invention achieves the possibility of simply and efficiently adapting the implant to the particular requirements of the surrounding tissue by forming a directional pore structure. At the same time, an implant which is produced by the process according to the invention is characterized by mechanical stability and biological compatibility. Furthermore, it can be produced in a great variety of geometrical shapes and thus also be employed in pharmaceutical and cosmetic applications, and in tissue reconstruction, in addition to other areas of use.

The process offers the possibility of producing readily resorbable implants, containing only a small proportion of foreign material, in a few steps and without any extensive technical or material input.

The quantities of material to be used, in particular the quantities of protein matrix, can be calculated precisely, which means that unnecessary consumption of material is avoided. This also makes it possible to set the desired layer thickness of the implant at the same time. The process can be used to produce thicknesses of the protein matrix layer of between 0.1 and 5 cm.

The formation of a desired pore structure can readily be calculated and achieved using simple means, such that the elaborate construction of master plates, for example, is dispensed with, with this having the advantage of a considerable saving in time and cost.

Other advantages ensue from the description and the attached drawing.

It goes without saying that the features, mentioned above, and those which are still to be explained below, can be used not only in the combination which is in each case specified but also in other combinations, or on their own, without departing from the scope of the present invention.

BRIEF DESCRIPTION OF THE DRAWINGS

Embodiments of the invention are depicted in the drawing and are explained in more detail in the subsequent description.

DETAILED DESCRIPTION OF PREFERRED EMBODIMENTS

Figure 1:
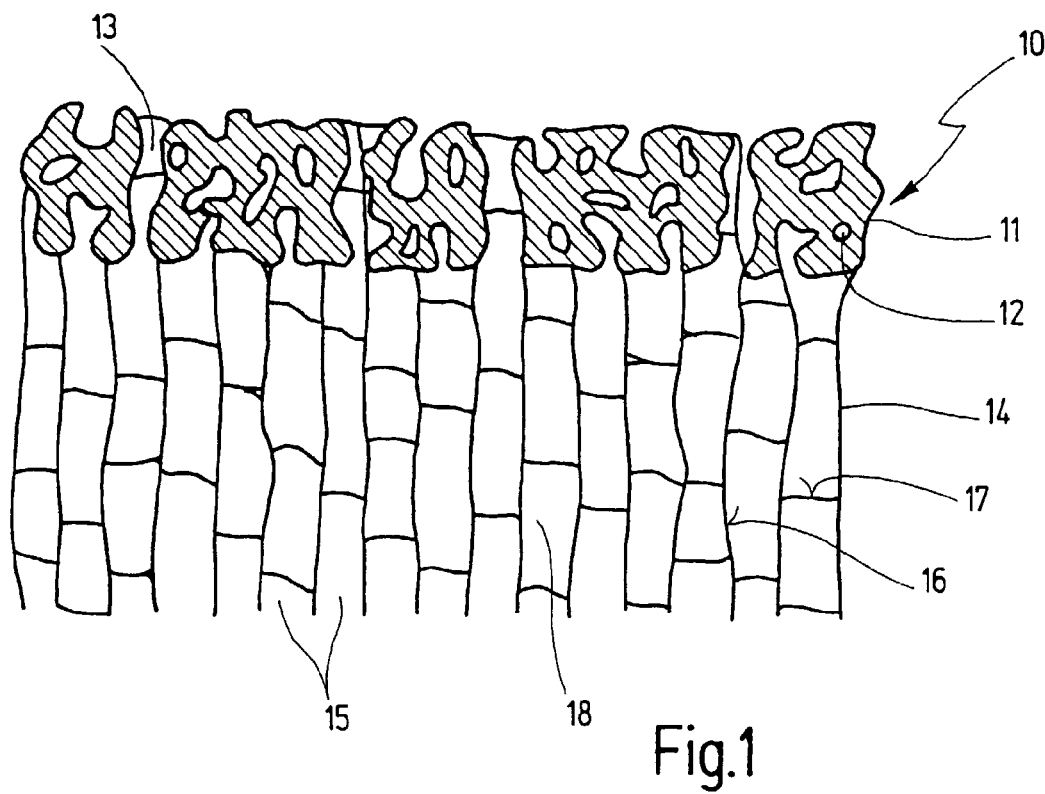
FIG. 1 shows a detailed sectional view of an embodiment of an implant according to the invention.

In FIG. 1, 10 designates the entirety of an implant having an internal foreign structure 11 with closed pores 12 and continuous or interconnected pores 13 and, in addition, having an outer protein matrix 14, which consists of long protein fibers 15. The protein fibers 15 are present in thin protein films 16 and individual short protein fibers 17 which together form pores 18.

During the production process, the protein matrix 14 becomes anchored in the inner foreign structure 11, which is textured by the closed and continuous pores 12 and 13. The protein matrix 14 consists of covalently crosslinked protein fibers 15 which, because of the production process, which is still to be described, and the anisotropy of ice, form very thin protein films 16 and are linked to each other by means of individual short protein fibers 17. The continuous pores 13 of the foreign structure 11 are large as compared with the pores 18 of the protein matrix 14 which means that the structure of the protein matrix 14 can continue unimpeded in the pores 13 of the foreign structure 11. The protein matrix 14 is stabilized towards mechanical stresses by its direct linkage to the foreign structure 11. Cells and liquids can be taken up in the pores 18 of the protein matrix 14, with the protein film 16 and the short protein fibers 17 forming adhesion surfaces for the cells in this connection. When collagen is used as a protein constituent, the cells which have become attached can remodel the resorbable support material into endogenous extracellular matrix.

Figure 2:
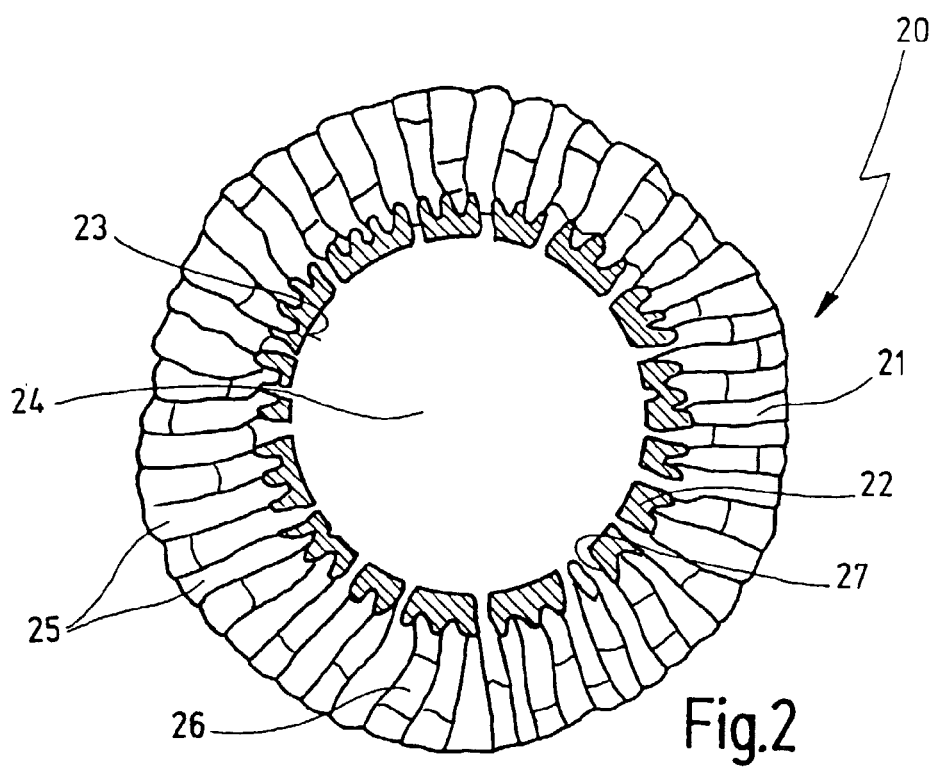
FIG. 2 shows a cross section through another embodiment of an implant according to the invention, namely a vascular graft.

FIG. 2 shows a vascular graft 20 which was produced using the process according to the invention. In this implant, a protein matrix 21 is deeply anchored in a foreign structure 22. An internal wall 23 of the vascular graft 20 forms the boundary to the lumen 24. The protein matrix 21 consists of protein fibers 25 possessing pores 26. The protein fibers are in direct contact with the lumen 24 by way of continuous pores 27 in the foreign structure 22.

The foreign structure 22 imparts adequate stability to the vascular graft 20. Cells, such as fibroblasts, can grow rapidly into the pores 26, which run in a directional manner, of the protein matrix 21. In addition, the internal wall 23 of the vascular graft 20 can be seeded with endothelial cells in order to avoid the graft being thrombogenic.

At this point, it should be noted that the vascular graft 20 shown in FIG. 2 only represents one embodiment. Apart from this, the invention can also be employed in other shapes and functions, such as patches in connection with skin implants, as cylinders or rectangles in connection with cartilage and bone implant, or heart valves.

The process can be used to produce implants in which the thicknesses of the protein matrix layer are different. A specific temperature course is applied for achieving a specific protein matrix layer thickness.

Figure 3:
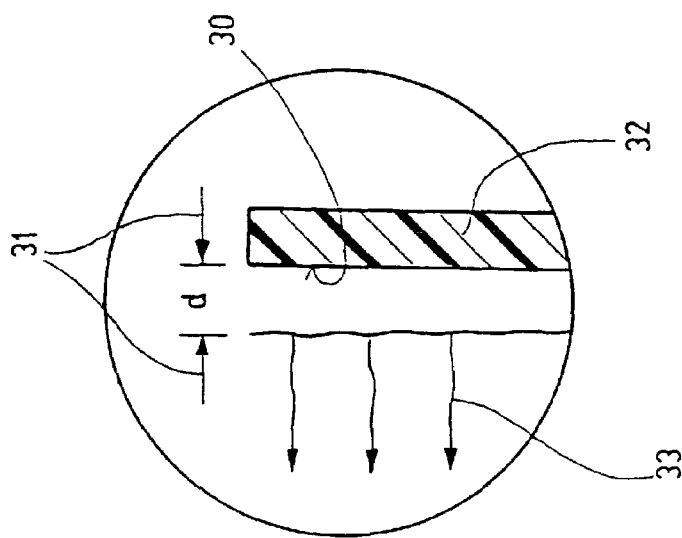
FIG. 3 shows an example of the course of the temperature when the temperature is regulated on one side.
Figure 3:
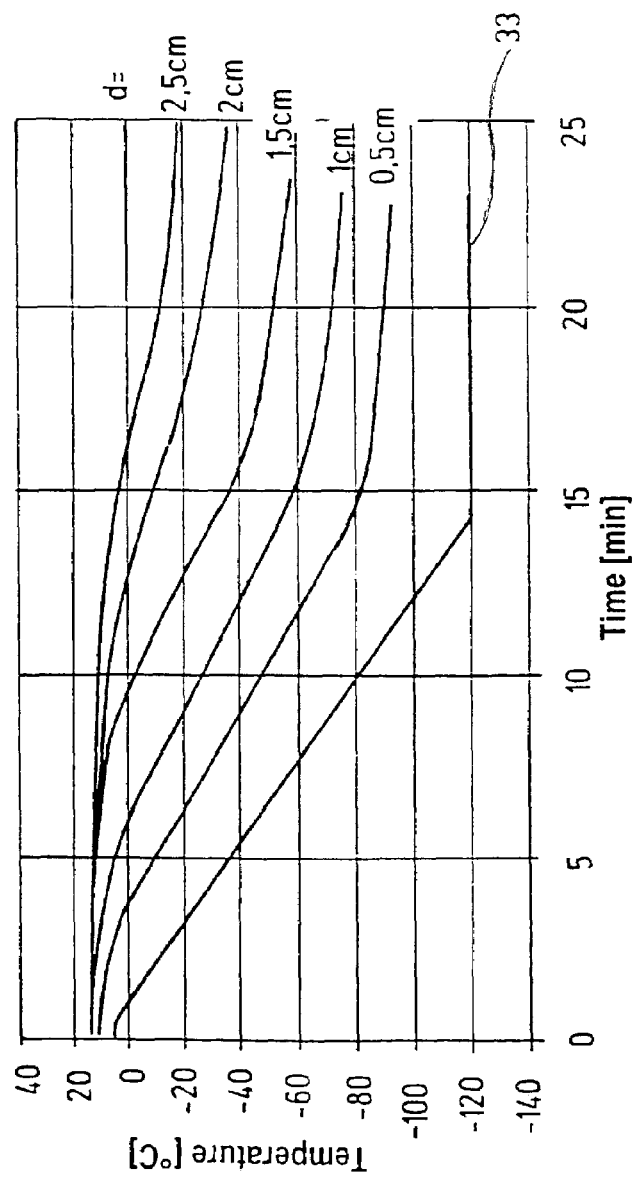

FIG. 3 shows the temperature course, plotted against time, when a collagen suspension is cooled at a constant rate of −9 K/min in various layer thicknesses. The temperature courses were measured in the following layer thicknesses d: 2.5; 2; 1.5; 1 and 0.5 cm. The measuring point 30 for the temperature courses is depicted schematically in the detail on the right alongside the diagram. The region d defined by the arrows 31 indicates the thickness of the protein matrix layer (in this case consisting of collagen). 32 depicts a synthetic material which serves as the foreign structure. The arrows 33 indicate the direction of cooling. Thus, for a wall thickness of 1 cm, for example, between 10 and 15 min are required in order to reach −50° C. The lowest curve 33 in the diagram shows the temperature course for wall thicknesses of <1 mm. By extrapolation, a cooling time of 5–10 min for reaching −50° C. is to be expected in the case of these wall thicknesses. Under these conditions, ice crystals of a size of approx. 35 μm in diameter grow through the collagen suspension.

Figure 4:
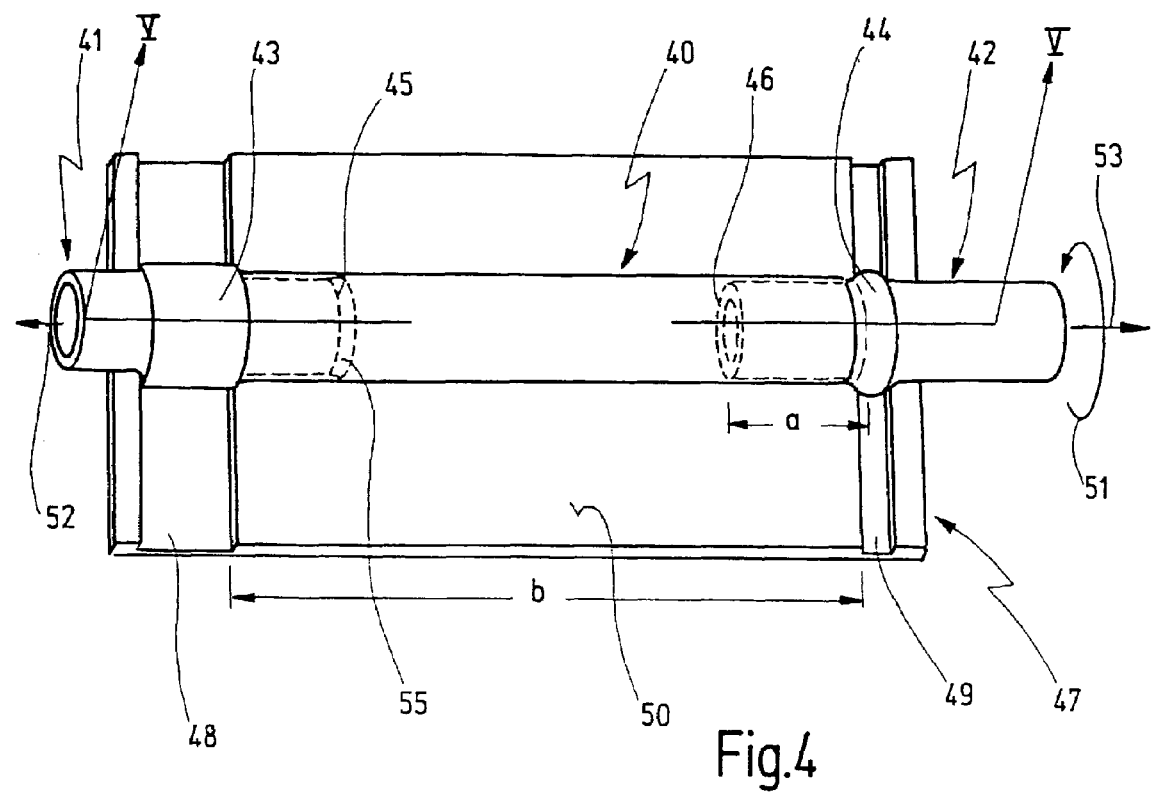
FIG. 4 shows a device for producing an implant having a directional pore structure.

FIG. 4 shows a device for producing an embodiment of the process according to the invention, namely a vascular graft. A tubular, prefabricated foreign structure 40 is mounted, at its ends, on two metal tubes 41 and 42, with a ring 43 being attached to the metal tube 41 and the metal tube 42 having a flange 44. The ring 43 and the flange 44 are in each case spaced at a particular distance a from the end of the metal tubes 45 and 46.

The device also exhibits a film 47, which possesses continuous recesses 48 and 49 whose dimensions correspond to the ring 43 and the flange 44. The distance b between the recesses corresponds to the length of the arrangement consisting of the ring 43 and the flange 44 and the foreign structure 40 which is mounted in between. The film 47 can be coated with a protein suspension on its surface 50 lying between the recesses 48 and 49 and subsequently wound around the arrangement consisting of metal tubes 41, 42 and the foreign structure 40 mounted in between, as indicated by an arrow 51. The metal tubes 41 and 42 can be connected, by way of their respective free ends, to a vacuum pump, as shown by the arrows 52 and 53.

Figure 5:
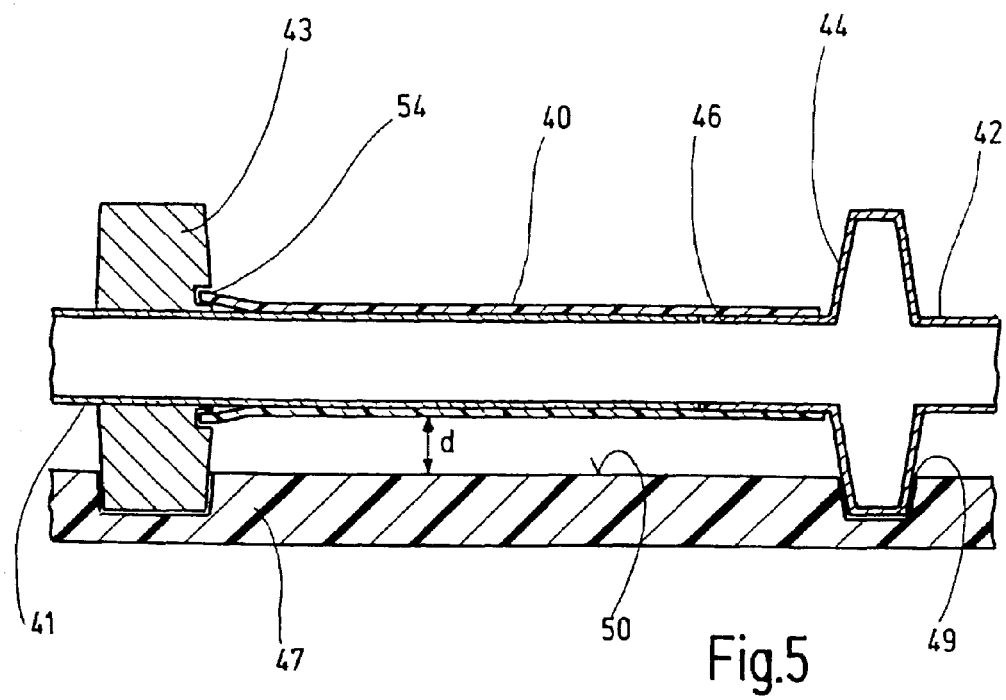
FIG. 5 shows an enlarged sectional view of the device from FIG. 4

FIG. 5 shows an enlarged sectional view of the device from FIG. 4. The same reference numbers as in FIG. 4 were used in so far as they relate to the same features.

The flange 44 of the metal tube 42 is introduced into the recess 49 of the film 47. The tubular foreign structure 40 is drawn over the end 46 of the metal tube 42. In the figure, the metal tube 41 is introduced, through the ring 43, into the tubular foreign structure 40 up to the end of the metal tube 46. Between the surface 50 of the film 47 and the tubular foreign structure 40, the thickness of the protein suspension layer, which thickness is determined by the distance of the film 47 from the tubular foreign structure 40, is indicated by d. This layer thickness can be adjusted at will by altering the depth of the recesses 48 and 49 or the length of the flange 44 and of the ring 43.

The use of the device is demonstrated with the aid of the example described below.

EXAMPLE

Producing a Vascular Graft According to the Invention

Known methods are used to produce a tubular foreign structure 40 which is composed of expanded polytetrafluoroethylene (ePTFE) having an internal diameter of 4 mm and a wall thickness of 100 μm. A very high porosity is achieved as a result of stretching, such that the mean pore size, determined by the distance between the PTFE nodes, is 60 μm.

The ends of the tube, whose total length is 340 mm, are in each case pushed, by 15 mm, onto concentrically double-lumened metal tubes 41, 42 having an external diameter of 4.1 mm. At a distance of 15 mm from its end 46, the metal tube 42 possesses a flange 44. A ring 43, which can be clamped on the tube using a socket, is located on the second tube. The ring 43 possesses a clamping device 54 with which one end of the foreign structure 40 can be clamped into the ring 43. The free ends of the metal tubes can be connected to a vacuum pump.

In parallel to this, an aqueous collagen suspension, having a viscosity of 8 Pa×s at 25° C., is prepared from 2% by weight insoluble collagen type 1, isolated from bovine hides, and 2% by weight ascorbic acid. The pH of the suspension is adjusted to 3.4 with hydrochloric acid. A scraper is used to apply this suspension, in a uniform layer thickness of 1 mm, to a rectangular film 47 having the dimensions 350 mm×19 mm.

The film 47 possesses adequate strength and consists, for example, of teflon. It is advantageous if the shorter sides of the film 47 are in each case provided with a recess 48, 49, the distance between which corresponds to that between the ring 43 and the flange 44, between which the tubular foreign structure 40 is mounted. In addition, the wall thickness of the sample can be specified by the depth of the recesses 48, 49 and by changing the flange 44 and the ring 43.

Subsequently, the ring 43 and the flange 44 of the metal tubes 41, 42 are placed in the recesses 48, 49 of the collagen suspension-coated film 47 and the film 47 is wound, on a level table, around the arrangement consisting of the tubular foreign structure 40 and the metal tube connections. This thereby generates a form for the vascular graft which is to be fabricated, with the flange 44 and the ring 43 as the end limit and the film 47 as the perimeter and simultaneous insulating layer. After that, the metal tubes are connected by their free ends to a vacuum pump. The vacuum pump is used to apply a slight negative pressure of 100 mbar and the suspension is sucked into the pores of the ePTFE tube. The one metal tube 41, which has an outer diameter of 4 mm, is then pushed through the ring 43 up to the end of the other metal tube 46. A seal 55 is located at the end of the metal tube 41, with this seal ensuring that no cooling liquid can escape at this connecting point (metal tube 41 to metal tube 42).

Subsequently, the collagen suspension is solidified, in a directional manner, by means of a unilaterally controlled freezing process. For this, the temperature of the metal tube 41, which now functions as the cooling tube, is lowered from room temperature (approx. 25° C.) down to −50° C. at a constant cooling rate of 6 K/min. The cooling medium employed is isopropanol; in order to ensure a more uniform temperature distribution along the metal tube, the cooling medium is separated, and in reverse flow, returned to the thermostat through the two concentrically arranged lumina.

Following freezing, the film 47 is removed. The specimens are stored at −70° C. for at least 12 h and subsequently freeze-dried. In this connection, the condenser temperature is kept at −85° C. until the water content of the resulting collagen matrix is <10% by weight. The collagen matrix is then removed from the form and subjected, at a negative pressure of $5 \times 10^{-5}$ bar and for approx. 14 h, to a temperature of 106° C. in order to crosslink the collagen dehydrothermally.

The ends of the specimens are then detached, in each case at a distance of 20 mm from the edge of the specimen.

After a subsequent sterilization, the vascular graft which has been produced by the process according to the invention, and which consists of collagen with ePTFE reinforcement, is ready for being seeded with myofibroblasts and endothelial cells in a cell reactor.

The invention claimed is:

1. A method for producing an implant having a textured foreign structure and, at least partially anchored therein, a porous protein matrix layer having a substantially unidirectional and homogeneous pore structure from one to the other of the two faces of the layer, the method comprising the steps of:
    A. providing a textured foreign structure, and an aqueous suspension, dispersion or paste which contains insoluble collagen and non-collagenous, soluble constituent(s) that are any one or more of acids, glycerol, ethanol, growth factors, extracellular matrix components, hirudin, aspirin, heparan sulphate, or albumin;
    B. applying the suspension, dispersion or paste to the textured foreign structure;
    C. introducing, at least partially, the suspension, dispersion or paste into the textured foreign structure by means of pressure, vacuum or centrifugation, to form a collagenous layer having a first surface and a second surface, the first surface being the lower or inner face and the second surface respectively being the upper or outer face of the layer; and
    D. freezing the layer by unilaterally cooling it by contacting one, but not both, of the two surfaces with a cooling agent, to form a temperature gradient between the two surfaces, and changing the temperature of the cooling agent in contact with said one surface at least once in a continuous manner during the freezing, until said cooling produces ice crystals that are substantially perpendicular to the cooling agent-contacted surface, whereby the layer is frozen.

2. The method according to claim 1, wherein the textured foreign structure employed is a resorbable synthetic material which is selected from the group consisting of polylactide, polyglycolic acid, polyhydroxyalkanoates and their copolymers.

3. The method according to claim 1, wherein the size of the pores of the protein matrix which are formed is between 5 μm and 500 μm.

4. The method according to claim 1, wherein the protein matrix is freeze-dried after having been cooled.

5. The method according to claim 1, wherein the thickness of the protein matrix layer which is formed is between 0.1 and 5 cm.

6. The method according to claim 1, wherein the implant is sterilized after having been freeze-dried.

7. The method according to claim 1, wherein the implant is seeded with cells prior to implantation.

8. The method according to claim 1, wherein, prior to implantation, the implant is loaded or coated with an active compound which is selected from the group consisting of hirudin, aspirin, heparin sulphate and albumin.

9. An implant having a textured foreign structure and a porous protein matrix layer which is at least partially anchored therein and which possesses a substantially unidirectional and homogeneous pore structure, from one to the other of the two faces of the layer, wherein the implant is produced by the method of claim 1.

10. The method according to claim 1, wherein said continuous changing of the temperature of the cooling agent involves decreasing the temperature thereof.

11. The method according to claim 1, wherein the textured foreign structure is a stable synthetic material selected from the group consisting of polytetrafluoroethylene, polyurethane, polystyrene, polyester, ceramic and metal.

12. The method according to claim 1, wherein the textured foreign structure is a natural material selected from the group consisting of chitin, cellulose, collagen, hydroxylapatite and calcium phosphate.

* * * * *

UNITED STATES PATENT AND TRADEMARK OFFICE
CERTIFICATE OF CORRECTION

PATENT NO. : 7,175,852 B2
APPLICATION NO. : 10/191674
DATED : February 13, 2007
INVENTOR(S) : Robert Simmoteit et al.

It is certified that error appears in the above-identified patent and that said Letters Patent is hereby corrected as shown below:

Title Page,
Item [75] Inventors, second line, "Heike Fisher geb. Schoof" should be -- Heike Fischer geb. Schoof --.
Item [73] Assignee, "Hechigen (DE)" should be -- Hechinger (DE) --.

Signed and Sealed this

Seventh Day of August, 2007

JON W. DUDAS
*Director of the United States Patent and Trademark Office*